(12) United States Patent
Hayball

(10) Patent No.: US 10,098,605 B2
(45) Date of Patent: Oct. 16, 2018

(54) SYNCHRONOUS PHYSIOLOGICAL MEASUREMENTS FOR CARDIAC ACQUISITIONS

(71) Applicant: SIEMENS MEDICAL SOLUTIONS USA, INC., Malvern, PA (US)

(72) Inventor: Julian Hayball, Oxfordshire (GB)

(73) Assignee: Siemens Medical Solutions USA, Inc., Malvern, PA (US)

(*) Notice: Subject to any disclaimer, the term of this patent is extended or adjusted under 35 U.S.C. 154(b) by 291 days.

(21) Appl. No.: 14/766,662

(22) PCT Filed: Feb. 6, 2014

(86) PCT No.: PCT/EP2014/052374
§ 371 (c)(1),
(2) Date: Aug. 7, 2015

(87) PCT Pub. No.: WO2014/122236
PCT Pub. Date: Aug. 14, 2014

(65) Prior Publication Data
US 2015/0359500 A1 Dec. 17, 2015

(30) Foreign Application Priority Data
Feb. 7, 2013 (GB) .................. 1302183.7

(51) Int. Cl.
A61B 6/00 (2006.01)
A61B 6/03 (2006.01)
A61B 5/021 (2006.01)
A61B 5/0275 (2006.01)
(Continued)

(52) U.S. Cl.
CPC .......... *A61B 6/5294* (2013.01); *A61B 5/0044* (2013.01); *A61B 5/021* (2013.01); *A61B 5/0275* (2013.01); *A61B 6/037* (2013.01); *A61B 6/486* (2013.01); *A61B 6/503* (2013.01); *A61B 6/507* (2013.01); *A61B 6/5217* (2013.01); *A61B 6/54* (2013.01); *A61B 5/024* (2013.01); *A61B 5/7278* (2013.01); *A61B 5/7282* (2013.01); *A61B 6/5288* (2013.01)

(58) Field of Classification Search
None
See application file for complete search history.

(56) References Cited

U.S. PATENT DOCUMENTS

| 8,428,220 B2 | 4/2013 | Buijns et al. |
| 8,897,518 B2 | 11/2014 | Solf et al. |
| 2004/0260178 A1 | 12/2004 | Kahn et al. |

(Continued)

OTHER PUBLICATIONS

Nagamachi et al., "Reproducibility of Measurements of Regional Resting and Hyperemic Myocardial Blood Flow Assessed with PET",The Journal of Nuclear Medicine, 1996; 37. pp. 1626-1631.*

(Continued)

*Primary Examiner* — James Kish
(74) *Attorney, Agent, or Firm* — Steven H. Noll

(57) ABSTRACT

In a method for acquiring medical data, a frame of SPECT or PET patient image data is acquired while simultaneously recording measurements of one or more physiological characteristics, synchronously with the capture of the frame of SPECT or PET patient image data. The measurements of one or more physiological characteristics are stored in association with the corresponding patient image data.

3 Claims, 2 Drawing Sheets

(51) Int. Cl.
    *A61B 5/024*        (2006.01)
    *A61B 5/00*         (2006.01)

(56) References Cited

U.S. PATENT DOCUMENTS

| | | |
|---|---|---|
| 2005/0023471 A1 | 2/2005 | Wang et al. |
| 2007/0055145 A1 | 3/2007 | Zelnik et al. |
| 2007/0100225 A1 | 5/2007 | Maschke |
| 2008/0033291 A1 | 2/2008 | Rousso et al. |
| 2008/0081980 A1 | 4/2008 | Maschke et al. |
| 2008/0131362 A1* | 6/2008 | Rousso ............... A61B 5/417 |
| | | 424/1.11 |
| 2010/0290683 A1 | 11/2010 | Demeester et al. |
| 2011/0178359 A1* | 7/2011 | Hirschman ............ G21F 5/015 |
| | | 600/4 |
| 2012/0035435 A1 | 2/2012 | Choi et al. |

OTHER PUBLICATIONS

Pan et al., Cardiac Positron Emission Tomography: Overview of Myocardial Perfusion, Myocardial Blood Flow and Myocardial Flow Reserve Imaging, Siemens Internet Publication, Nov. 1, 2011.
Efseaff et al., "Short-Term Repeatability of Resting Myocardial Blood Flow Measurements Using Rubiudium-82 PET Imaging," Journal of Nuclear Cardiology, Vo. 19, No. 5 (2012), pp. 997-1006.
Chareonthaitawee et al., "Heterogeneity of Resting and Hyperemic Myocardial Blood Flow in Healthy Humans," Cardiovascular Research, vol. 50, No. 1 (2001) pp. 151-161.

\* cited by examiner

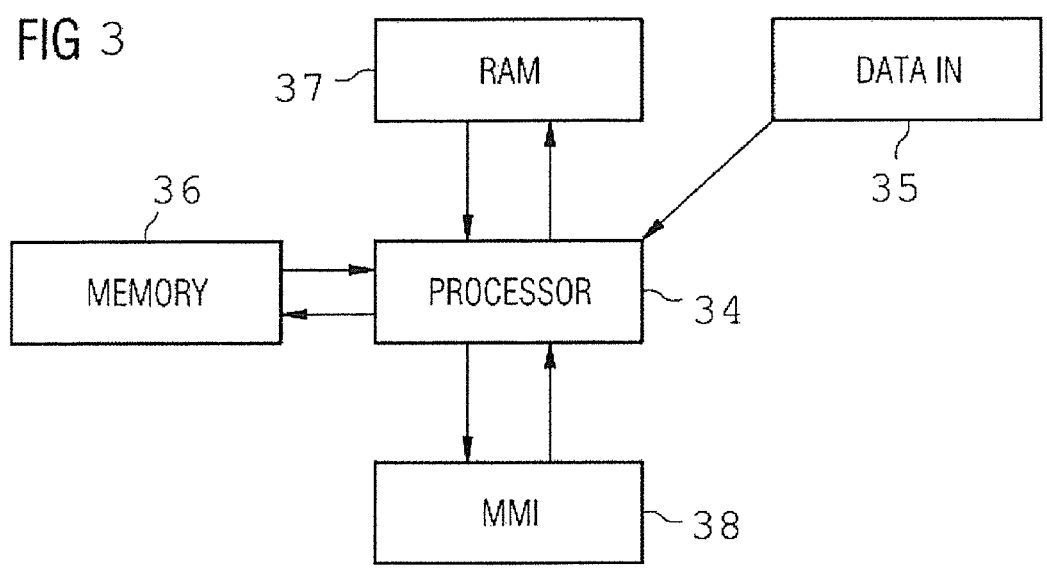

SYNCHRONOUS PHYSIOLOGICAL MEASUREMENTS FOR CARDIAC ACQUISITIONS

BACKGROUND OF THE INVENTION

Field of the Invention

The present invention concerns a method and apparatus for acquiring medical imaging data and for correlating the acquired medical imaging data with measurements of physiological characteristics of a patient.

Description of the Prior Art

In the diagnosis of Coronary Artery Disease (CAD), molecular imaging techniques are used to measure blood flow in the myocardium. Radiopharmaceuticals that act as tracers for blood are introduced into the patient and imaged using Single Photon Emission Computed Tomography (SPECT) or Positron Emission Tomography (PET) scanners.

In images produced by PET or SPECT scans, the myocardium shows up as a region of high activity where blood is being carried through the coronary arteries and into the wall of the heart. Areas of reduced flow are possible indicators of coronary vessel stenosis, which is characteristic of CAD.

In many cases, acquisitions are repeated both under conditions of rest and of stress. Measurement of blood flow under each may enhance the information available to the clinician. A condition of stress may be induced by exercising the patient on, for example, an exercise bike, or may be induced pharmaceutically.

One established technique for detecting disease in this domain is to compare measurements of blood flow in the patient under examination with a database of "normal" cases representing similar measurements on healthy individuals. This technique assists the physician in assessing whether detected variations in measured blood flow are clinically significant. The compared measurements, however, typically represent relative blood flow, which renders such comparison less than ideal.

A dynamic scan protocol involves acquisition of a number of time-stamped SPECT or PET images of the heart at different timepoints over a period of time. From a collection of such time-stamped images, one can determine the rate at which the tracer has entered different regions of the myocardium. Using kinetic modeling techniques known in themselves, this information can be used to derive measurements of absolute blood flow at particular times, which allows a more direct and meaningful comparison between the patient data acquisition and databases of "normal" cases.

A problem with this methodology is that the derived absolute blood flow rate is calculated only from a rate of change of SPECT or PET activity in the myocardium. Real absolute blood flow rate is also dependent on the patient's heart rate and blood pressure as well as blood vessel diameter at the time of acquisition. Various techniques are used to normalize the derived blood flow measurements against variations in these parameters.

However, such techniques involve the measurement of the relevant parameters—in this case, heart rate, blood pressure and vessel diameter—prior to, and/or after, the patient SPECT or PET data acquisition. No account is taken of changes in the values of these parameters between the time of their measurement and the time of the patient SPECT or PET data acquisition, which may, especially in the case of a stress scan, be a significant time.

A patient's Heart Rate (HR) and Blood Pressure (BP) may vary significantly over the course of the patient SPECT or PET data acquisition, particularly in the case of a dynamic cardiac acquisition, which may take many minutes. This variation will bias the results to emphasize data corresponding to time periods of higher blood pressure and heart rate.

SUMMARY OF THE INVENTION

In a method and apparatus according to the invention, a SPECT or PET scanner is operated to acquire a frame of SPECT or PET patient image data of a patient situated in the scanner, while simultaneously acquiring measurements of one of more physiological characteristics of the patient. The measurements of the one or more physiological characteristics are stored in an electronic memory in association with the corresponding patient image data.

BRIEF DESCRIPTION OF THE DRAWINGS

FIG. 3 schematically illustrates a computer system according to the present invention.

DESCRIPTION OF THE PREFERRED EMBODIMENTS

Figure 1:
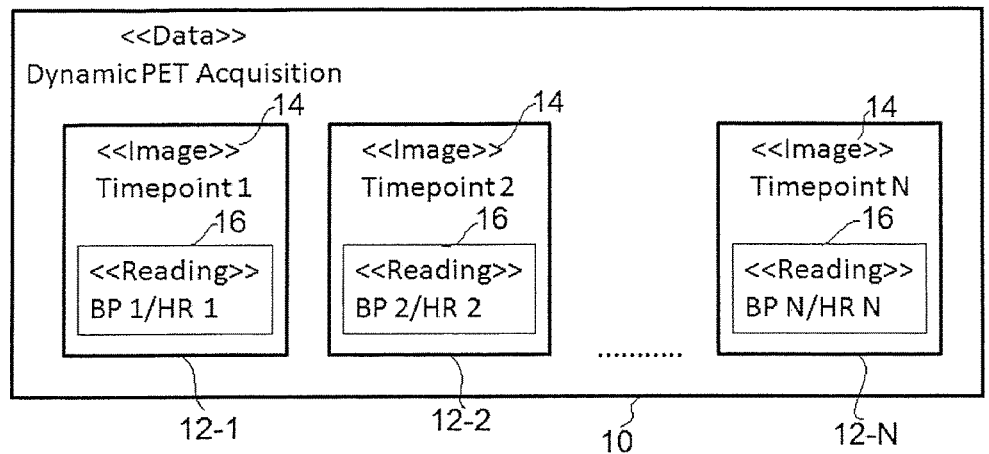
FIG. 1 illustrates a data model for dynamically acquired PET data with synchronous blood pressure and heart rate measurements.

According to an aspect of the invention, a device to measure BP and HR is provided, associated with and preferably integrated into a SPECT or PET scanner. In operation, under cardiac protocols, that is to say with the SPECT or PET scanner configured to support imaging of the heart and allowing blood flow analysis, measurements of HR and/or BP are made, synchronous with respective SPECT or PET acquisitions. The HR and/or BP measurements are each recorded in the scanner's data output, associated with the corresponding SPECT or PET image data acquisition.

In the case of a dynamic cardiac acquisition, synchronous BP and/or HR measurements by the relevant device are triggered by the SPECT or PET scanner at each image data frame capture timepoint. The results of each measurement are stored, associated with each corresponding frame of the dynamic SPECT or PET image data output, each frame then consisting of one more sets of image data along with numeric data representing the BP and HR as measured synchronously, at the time of acquisition of the associated SPECT or PET image data frame(s). The acquired BP and HR information may be recalled and used in post processing of the image data, for example in order to allow improved comparison against databases of "normal" cases, or to remove a bias towards timepoints of high blood pressure and high heart rate from dynamic acquisitions. Calculated measurements of absolute blood flow rate may be improved by the removal of such bias. In addition to comparison against a database of equivalent data for healthy individuals, the normalized patient data may be compared against equivalent data for individuals known to be suffering from certain affliction, to assist with diagnosis of the present patient.

The present invention may relate to use of measurement equipment which is capable of recording blood pressure (BP) and heart rate (HR), and to use of measurement equipment which measures only one of these characteristics, and/or, one or more others. Removal of bias according to the present invention may only be performed in respect of the measured characteristic(s). Alternatively, a likely value of one or more unmeasured characteristic(s) may be derived for a patient, based on one or more measured characteristic(s) and previously-acquired correspondence between the measured and unmeasured characteristics, such as blood pressure and heart rate, for that patient; or for a general patient.

The measurement of physiological parameters such as HR or BP at the same time, or at about the same time, as patient image data capture is, in itself, known in other contexts. The present invention provides synchronous measurement of physiological parameters such as HR or BP at the time of patient image data capture at the timepoint of capture for each frame, and the measurements recorded in association with the corresponding image frame data. On post processing of the image data, according to the present invention, absolute blood flow rate measurements are normalized, typically by correcting to a standard HR and BP, so that they can be compared with a database of similarly normalized values for "normal" cases representing similar measurements on healthy individuals. This enables interpretation of captured patient images by normalizing or removing bias caused by variation in patient heart rate or blood pressure. Conventional arrangements provided recording of heart rate and/or blood pressure for patient monitoring and evaluation of patient response to treatment. In conventional arrangements, ECG data or similar is used for "gating" image data acquisition to a certain point in a heartbeat cycle, the ECG data is typically unused, and usually discarded.

The present invention particularly related to dynamic acquisition, in which multiple SPECT or PET data sets are captured, in relatively rapid succession, of a certain region of interest. In the case of a dynamic imaging sequence, image data frames may be captured over a period of several minutes. The change in tracer concentration revealed in these data sets allows a blood flow rate to be calculated. By associating synchronous physiological measurements such as HR or BP with corresponding image frame data, the calculated blood flow rates may be normalized to reduce the influence of variation in the measured physiological characteristic(s). As the physiological measurement data is linked with, and preferably incorporated within, the image data set, normalization and compensation for variation in the measured physiological characteristic(s) may be performed during post-processing of the image data. The present invention does not use physiological measurements to time the image data capture, but rather employs physiological measurements which are captured synchronously with image data frame capture.

Preferably, in apparatus according to the present invention, blood pressure (BP) and/or heart rate (HR) measurements are activated by the Single Photon Emission Computed Tomography (SPECT) or Positron Emission Tomography (PET) scanner as part of an acquisition protocol, and the measurement data stored with the corresponding image frame data.

FIG. 1 schematically illustrates a data structure 10 for dynamically acquired SPECT or PET data with synchronous BP and/or HR measurements, according to an aspect of the present invention. Dynamic PET acquisition data set 10 includes multiple data frames, 12-1, 12-2 to 12-N, each representing a data acquisition timepoint. The data set 10 will be captured over an imaging session typically lasting several minutes, and each data frame 12 will represent data captured at a respective timepoint.

In each data frame 12, a frame of image data 14, captured by PET or SPECT, is accompanied by a reading 16 representing a measurement of one or more physiological characteristics, such as HR or BP captured synchronously with the image data of that data frame.

Data set 10 may be stored in this state, and may later be processed by a post-processing means and method which extracts the frame of image data and uses the corresponding reading 16 to compensate the blood flow rates indicated by the image frame data for variation in the physiological characteristics. The physiological measurements can be recalled at the post-processing stage for the purposes of normalization or bias correction.

Figure 2:
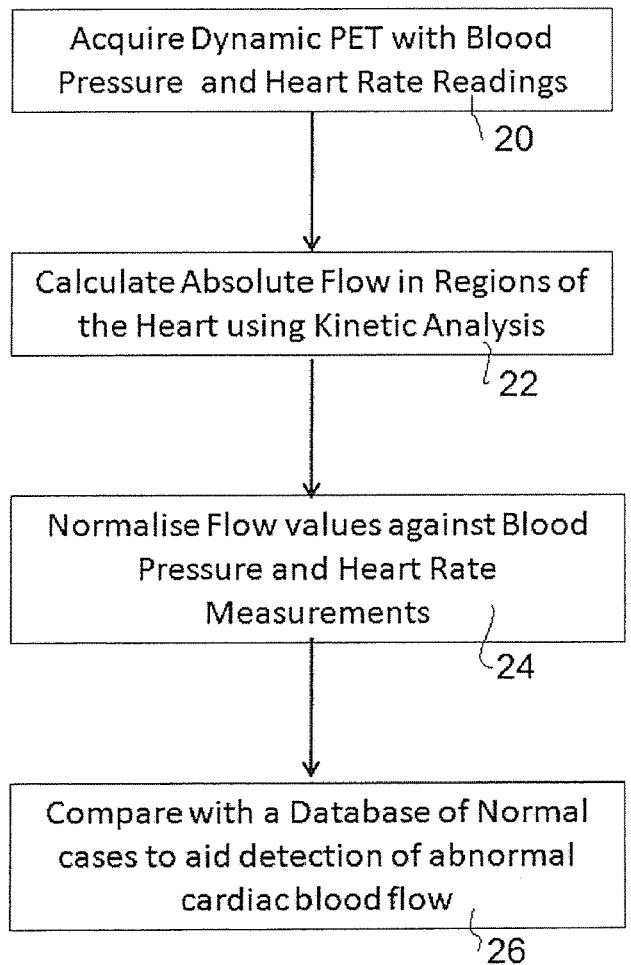
FIG. 2 shows a flow diagram for using synchronous blood pressure and heart rate measurements in normalizing blood flow calculations for the purpose of improving comparison with databases.

FIG. 2 is a flow diagram of a method using synchronous BP and HR measurements in normalizing blood flow calculations for the purpose of improving comparison with databases. It schematically illustrates a method according to an aspect of the present invention. In step 20, dynamic SPECT or PET data image frames are recorded, along with synchronous measurements of one or more physiological characteristics such as HR or BP. The physiological measurements are carried out at the timepoint of image data acquisition by a device which is activated by the SPECT or PET scanner as part of its acquisition protocol. The measurements are stored with the image data, for example in a data structure such as that illustrated in FIG. 1.

In step 22, the SPECT or PET image data frames are post-processed to calculate absolute blood flow rates in the imaged region of interest, for example the heart.

In step 24, the calculated absolute blood flow rates calculated in step 22 are normalized to reduce or eliminate the effect of variations in the measured physiological characteristics such as HR or BP. In some embodiments of the invention, steps 22 and 24 may be combined into a post-processing step which both calculates absolute blood flow rates in the imaged region of interest, and normalizes the calculated absolute blood flow rates to reduce or eliminate the effect of variations in the measured physiological characteristics such as HR or BP.

In step 26, the normalized absolute blood flow rates are compared with a database of values for "normal" cases representing similar measurements on healthy individuals. This may assist a physician in diagnosis of CAD.

The present invention accordingly provides methods in which BP and HR measurement such that during a dynamic acquisition in a SPECT or PET scanner under cardiac protocols, at each timepoint, the measurements are recorded with the image data acquired for that timepoint. On post processing the absolute blood flow measurements are normalized, that is they are corrected to a standard BP and HR, and compared with a similarly normalized database of normal cases. The resultant improved measurements of absolute blood flow rate improve comparability between blood flow data by correcting for the effect of variability in physiological characteristic s such as BP and HR between data sets.

Devices to measure physiological characteristics such as HR or BP may be integrated into a PET or SPECT scanner to facilitate synchronous measurement and data storage according to the present invention.

Referring to FIG. 3, an embodiment of the invention may be conveniently realized as a computer system suitably programmed with instructions for carrying out the steps of the methods according to the invention.

For example, a central processing unit 34 is able to receive data representative of medical scans via a port 35 which could be a reader for portable data storage media (e.g. CD-ROM); a direct link with apparatus such as a medical scanner (not shown) or a connection to a network.

For example, in an embodiment, the processor performs such steps as capturing a frame of SPECT or PET patient image data;

simultaneously recording measurements of one or more physiological characteristics, synchronously with the capture of the frame of SPECT or PET patient image data; and recording the measurements of one or more physiological characteristics in association with the corresponding patient image data.

Software applications loaded on memory 36 are executed to process the image data in random access memory 37.

A Man—Machine interface 38 typically includes a keyboard/mouse combination or equivalent (which allows user input such as initiation of applications) and a screen on which the results of executing the applications are displayed.

Although modifications and changes may be suggested by those skilled in the art, it is the intention of the inventor to embody within the patent warranted heron all changes and modifications as reasonably and properly come within the scope of his contribution to the art.

I claim:

1. A method for evaluating a cardiac status of a patient, comprising:

using a control computer to operate a SPECT or PET scanner in order to acquire multiple frames of SPECT or PET patient image data from a region in an examined patient to whom a radioactive tracer has been administered, during a data acquisition time comprising a plurality of minutes in a dynamic cardiac acquisition procedure, said multiple frames allowing determination of uptake of the tracer in different parts of said region, and time stamping each frame;

using said control computer to operate a physiological characteristic detector in order to make multiple measurements of a value of at least one physiological characteristic of the examined patient that exhibits a total change over said plurality of minutes, selected from the group consisting of blood pressure and heart rate, by triggering said physiological characteristic detector to make a measurement of said value of said at least one physiological characteristic during a respective measurement time that occurs in each of said multiple frames of said patient image data, thereby measuring said at least one physiological characteristic with a time resolution from frame-to-frame that is more precise that said plurality of minutes;

in a memory, storing the value of said at least one physiological characteristic respectively acquired during each of said frames of said patient image data, correlated by said time stamping with the respective frame of patient image data in which said measurement time of said value of said physiological characteristic occurred;

from a processor, accessing said patient image data from said memory and, in said processor, calculating, from the image data for each frame, a value of absolute blood flow rate in regions of the heart of the subject;

in said processor, using said value of said at least one physiological characteristic, measured during a respective frame, to normalize the absolute blood rate in said regions of the heart of the patient that was calculated for that respective frame;

in said processor, comparing the normalized absolute blood flow rate of the respective frames to respective values of absolute blood flow rate in a database of database patients each having a cardiac status, so as to produce a comparison result that indicates a cardiac status of examined said patient that corresponds to the cardiac status of at least one of the database patients, in order to produce an electronic designation of whether said examined patient has a cardiac-related affliction; and presenting said electronic designation as a humanly-perceptible output at an interface in communication with said processor.

2. An apparatus for evaluating a cardiac status of a patient, comprising:

a SPECT or PET scanner;

a physiological characteristic detector;

a memory;

a control computer having access to said memory;

a processor having access to said memory;

an output interface in communication with said processor;

said control computer being configured to operate the SPECT or PET scanner in order to acquire multiple frames of SPECT or PET patient image data from a region in an examined patient to whom a radioactive tracer has been administered; during a data acquisition time comprising a plurality of minutes in a dynamic cardiac acquisition procedure, said multiple frames allowing determination of uptake of the tracer in different parts of said region, and to time stamp each frame;

said control computer being configured to operate said physiological characteristic detector in order to make multiple measurements of a value of at least one physiological characteristic of the examined patient that exhibits a total change over said plurality of minutes, selected from the group consisting of blood pressure and heart rate, by triggering said physiological characteristic detector to make a measurement of said value of said at least one physiological characteristic during a respective measurement time that occurs in each of said multiple frames of said patient image data, thereby measuring said at least one physiological characteristic with a time resolution from frame-to-frame that is more precise that said plurality of minutes;

said control computer being configured to store, in said memory, the value of said at least one physiological characteristic respectively acquired during each of said frames of said patient image data, correlated by said time stamp with the respective frame of patient image data in which said measurement time of said value of said physiological characteristic occurred;

said processor being configured to access said patient image data from said memory and to calculate, from the image data for each frame, a value of absolute blood flow rate in regions of the heart of the subject;

said processor being configured to use said value of said at least one physiological characteristic, measured during a respective frame, to normalize the absolute blood rate in said regions of the heart of the patient that was calculated for that respective frame;

said processor being configured to compare the normalized absolute blood flow rate of the respective frames to respective values of absolute blood flow rate in a database of database patients each having a cardiac status, so as to produce a comparison result that indicates a cardiac status of said examined patient that corresponds to the cardiac status of at least one of the database patients, in order to produce an electronic designation of whether said examined patient has a cardiac-related affliction; and said processor being configured to present said electronic designation as a humanly-perceptible output at said output interface.

3. A non-transitory, computer-readable data storage medium encoded with programming instructions, said storage medium being distributively loaded into a control computer and a processor of a medical imaging system, said medical imaging system comprising a SPECT or PET scanner, a physiological characteristic detector, a memory, and an output interface, said programming instructions causing said control computer and said processor to:

with said control computer, operate the SPECT or PET scanner in order to acquire multiple frames of SPECT or PET patient image data from a region in an examined patient to whom a radioactive tracer has been administered, during a data acquisition time comprising a plurality of minutes in a dynamic cardiac acquisition procedure, said multiple frames allowing determination of uptake of the tracer in different parts of said region, and to time stamp each frame;

with said control computer, operate said physiological characteristic detector in order to make multiple measurements of a value of at least one physiological characteristic of the examined patient that exhibits a total change over said plurality of minutes, selected from the group consisting of blood pressure and heart rate, by triggering said physiological characteristic detector to make a measurement of said value of said at least one physiological characteristic during a respective measurement time that occurs in each of said multiple frames of said patient image data, thereby measuring said at least one physiological characteristic with a time resolution from frame-to-frame that is more precise that said plurality of minutes;

with said computer, store, in said memory, the value of said at least one physiological characteristic respectively acquired during each of said frames of said patient image data, correlated by said time stamp with the respective frame of patient image data in which said measurement time of said value of said physiological characteristic occurred;

from said processor, access said patient image data from said memory and, with said processor, calculate, from the image data for each frame, a value of absolute blood flow rate in regions of the heart of the subject;

with said processor, use said value of said at least one physiological characteristic, measured during a respective frame, to normalize the absolute blood rate in said regions of the heart of the patient that was calculated for that respective frame;

with said processor, compare the normalized absolute blood flow rate of the respective frames to respective values of absolute blood flow rate in a database of database patients each having a cardiac status, so as to produce a comparison result that indicates a cardiac status of said examined patient that corresponds to the cardiac status of at least one of the database patients, in order to produce an electronic designation of whether said examined patient has a cardiac-related affliction; and from said processor, present said electronic designation as a humanly-perceptible output at said output interface.

* * * * *